United States Patent [19]
Selby et al.

[11] Patent Number: 5,595,152
[45] Date of Patent: Jan. 21, 1997

[54] CLANDESTINE SAMPLING APPARATUS AND METHOD

[75] Inventors: Theodore W. Selby; Jerry G. Cox, both of Midland; Paul A. Bennett, St. Johns; Rebecca S. Cox, Midland, all of Mich.

[73] Assignee: The Saginaw Valley Institute of Materials, Inc., Midland, Mich.

[21] Appl. No.: 512,544

[22] Filed: Aug. 8, 1995

[51] Int. Cl.[6] .................................................. F01M 11/04
[52] U.S. Cl. ................... 123/196 R; 184/1.5; 73/864.91
[58] Field of Search ......................... 123/196 R, 196 AB; 184/1.5; 73/864.91

[56] References Cited

U.S. PATENT DOCUMENTS

| | | | |
|---|---|---|---|
| 3,603,155 | 9/1971 | Morris et al. | 73/864.91 |
| 4,869,346 | 9/1989 | Nelson | 184/1.5 |
| 5,130,014 | 7/1992 | Volz | 184/1.5 |
| 5,216,925 | 6/1993 | Odernheimer | 73/864.91 |
| 5,238,085 | 8/1993 | Engelmann | 184/1.5 |
| 5,263,445 | 11/1993 | Bedi et al. | 184/1.5 |
| 5,372,219 | 12/1994 | Peralta | 184/1.5 |

OTHER PUBLICATIONS

Communication to Mr. Pat Casey from Mr. Floyd Worcester, "Modified Valve Cover for Undercover Oil Changes," May 9, 1993.
Letter to from Ms. Rebecca Selby Cox, "Ref: Bulk Oil Project," Jan. 28, 1994.

*Primary Examiner*—Erick R. Solis
*Attorney, Agent, or Firm*—Christopher John Rudy

[57] ABSTRACT

A stationary or movable object suitable for holding a fluid can have the fluid sampled unobserved, and the sample is separate from the working and/or storage system(s) of the object. For example, an engine oil collection apparatus effectively collects engine oil during mimic of a normal oil change procedure, and allows for collection of samples without the sample going through the crankcase of the engine. The collected fluid, for example, the oil, can be set aside and/or analyzed for its composition afterwards.

15 Claims, 7 Drawing Sheets

CLANDESTINE SAMPLING APPARATUS AND METHOD

FIELD

This invention concerns a vehicle fluid or other object fluid collection apparatus and method, useful for collecting, unobserved, a sample of the fluid for analysis, to include as obtained from a service station. Engine oils are of particular concern.

BACKGROUND

The actual compositions of motor oils are of critical importance in engine performance. Ascertaining the actual compositions, of course, requires sampling for analyses.

Early engine oil compositions, as for example, in the U.S.A., were unregulated. Specifications affecting packaged engine oils have been progressively developed since the 1930's. However, even though packaged engine oil such as can be obtained in quart or gallon containers is regulated, bulk engine oil such as can be put into the car engine by quick-oil-change businesses, car dealers, or service stations remains unregulated, and is often the subject of concern regarding the quality of the product purchased by the business from suppliers of the business. Knowledge of actual compositions are of great importance both to the automobile manufacturers and to the engine oil manufacturing industry.

It is relatively easy, on the one hand, to obtain samples of packaged engine oil which reflect the actual and intended compositions thereof. One need only purchase a number of the packaged samples off a store shelf to do this.

On the other hand, it is often not so straightforward a procedure to obtain samples of bulk engine oil which reflect the actual and intended compositions thereof. First, bulk engine oil samples as available from engine oil service stations are generally dispensed into the motor vehicle engine directly, and not into separate containers such as would be useful for sampling. When dispensed into an engine the motor oil becomes contaminated or tainted by the old oil and so forth left behind in bearings and other lubricated moving parts, complex oil distribution lines, and in crankcase and valve cover areas in general, and thus, it is of little if any value for scientific analysis. Second, in cases of subterfuge or proprietary engine oil provision such as when a service station would label its visible oil drums with one type or brand of an oil but substitute a cheaper or less desirable type or brand or as when a supplier would not wish to divulge the compositions of its bulk oil supplies provided the public, engine oil service station attendants are loathe to provide engine oil to persons who would analyze the oil to ascertain its actual characteristics.

In addition, an unscrupulous service station operator may tell a customer that he is filling a customer's engine with one type or brand of an oil, whether it be bulk or packaged, but substitute a less desirable type or brand. In such a case as well, the attendant would be unlikely to provide the actual identity of the oil by word or by sample.

In an attempt to address such problems, the State of California has developed a modified valve cover for under cover oil changes, in which a valve cover is modified by increasing its height an inch, and by welding in a baffle plate having an upstanding overflow tube through which oil descends into the working valves and then the lower parts of the engine. The cover can collect only about a quart of oil, and the collected oil is exposed to fumes and heat of the engine through the overflow tube, which is not closed off from the working parts of the engine.

As yell, similar considerations may apply to other vehicle fluids.

It would be desirable to overcome such problems as these and effectively sample oil or other fluid for analysis. It would also be desirable to provide efficient, relatively-inexpensive, and simple-in-manufacture-and-operation ways and means thereof.

SUMMARY

The invention provides, in one aspect, a clandestine engine oil sampling apparatus comprising a motor vehicle engine with the following components: an oil entry port in mimic of an oil entry port or the motor vehicle engine into which a sample of motor oil can be dispensed; an entry shunt in communication with the entry port, through which the sample of motor oil can travel upon entry through the entry port and bypass lubricated moving parts in the motor vehicle engine; and an entry reservoir in communication with the entry shunt, in which the sample of motor oil can be stored upon travel through the entry shunt. The apparatus may also have an exit port in mimic of an oil exit port of the motor vehicle engine from which an expendable motor oil portion can drain; an exit shunt in communication with the exit port, through which the expendable motor oil portion can flow to the exit port apart from any working motor oil supply of the motor vehicle engine; and an exit reservoir in communication with the exit shunt, in which the expendable motor oil portion can pass through into the exit shunt and at least a portion or which can be stored for release into the exit shunt; and/or a dipstick fill indicator device having a dipstick and dipstick sheath in mimic of a dipstick fill indicator device of the motor vehicle engine, with an oil reservoir in communication with a lower end of the dipstick sheath, which can be filled with oil and into which the dipstick can be inserted so as to indicate mock-filling of the motor vehicle engine with new oil. In a further aspect, a method for clandestinely sampling a motor oil comprises operation of an apparatus as of the invention. Further aspects include generalized sampling of vehicular fluids by application of the aforesummarized, in principle, to the fluid under consideration and the apparatus to do so. More generally, any suitable object might be so sampled.

The invention is useful in effective oil analysis. As can be also seen hereby, the invention is useful in analysis of other fluids, especially liquids.

Significantly, by the invention, oil samples as provided from service stations can be sampled with the attendant unaware of the sampling. Thus, oil collection can be carried out during mimic or a normal oil change procedure. The oil can be collected without contamination from vapors such as from unburnt fuel, combusted or partially combusted fuel and/or lubricants, and from excessive engine heat, and in such an uncontaminated or pristine state, it can be set aside and/or analyzed for its composition afterwards. And so, true samples of motor oils can be effectively obtained for analysis. The invention solves or ameliorates problems and satisfies desiderata in the art such as aforesaid, and notably, it is efficient, relatively inexpensive, and simple in manufacture and operation. It is generally applicable to the sampling of other fluids, from organics to potable water supplies.

Accordingly, a stationary or movable object suitable for holding a fluid can have the fluid sampled unobserved, and the sample is separate from the working and/or storage system(s) of the object. For example, an engine oil collection apparatus effectively collects engine oil during mimic of a normal oil change procedure, and allows for collection of samples without the sample going through the crankcase of the engine. The collected fluid, for example, the oil, can be set aside and/or analyzed for its composition afterwards.

Numerous further advantages attend the invention.

DRAWINGS

The drawings form part of the specification hereof. In the drawings, the following is briefly noted.

ILLUSTRATIVE DETAIL

The invention can be further understood by reference to the present detail and drawings, which are to be considered in an illustrative and not necessarily limiting sense.

Clandestine engine oil sampling apparatus 100 is made up of a working motor vehicle engine 10 modified to include oil entry port 20, into which sample oil 5 is filled, and in mimic of an oil entry port of the motor vehicle engine such as in exterior valve cover 21 having rotatable oil fill cap 22, and suitable receiving hole 23; and entry shunt 30, typically with other components including shunt line 34.

Figure 1:
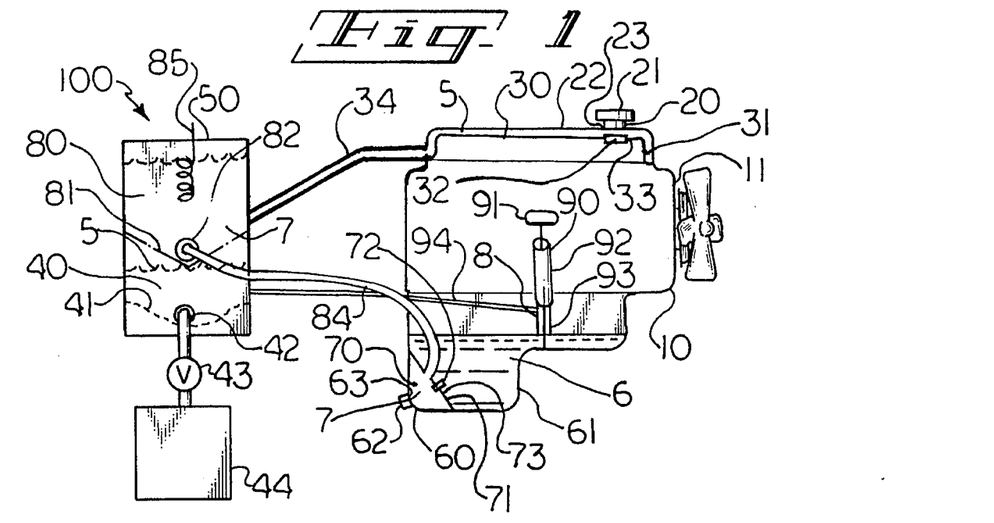
FIG. 1 is a general side view of a clandestine engine oil sampling apparatus of the invention.

In one embodiment, as depicted in FIG. 1, the entry shunt has interior, nested valve cover 31, made of a steel valve cover having an unobtrusive, removable fill plug 32 in fill plug hole 33, accessible for filling the engine 10 with working oil 6 by removing the exterior valve cover 21 in private, and which is bolted to engine head 11.

In a preferred embodiment, as depicted in FIGS. 9–12, the entry shunt 30 has interior, nested valve cover 31, made of a steel valve cover and which has PCV valve/oil-filling hole 35 to the engine 10 with the nested valve cover 31 otherwise inaccessible to the engine 10.

Such modifications effectively mimic normal engine oil filling arrangements in normal valve covers. An interior plate or nested valve cover generally appears to be a standard valve oil deflection plate to the unsuspecting service station attendant.

Figure 13:
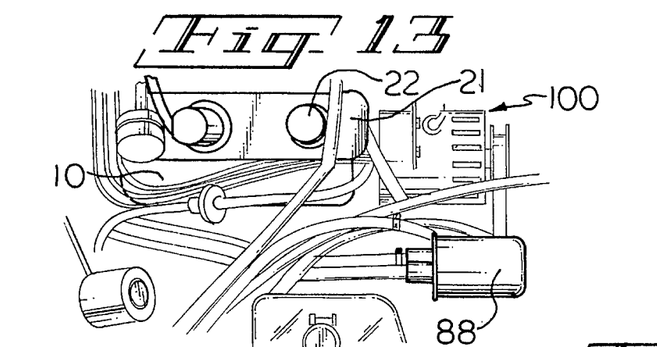
FIG. 13 is a perspective view of part of a clandestine engine oil sampling apparatus of the invention installed in the environment of a motor vehicle engine compartment.
Figure 14:
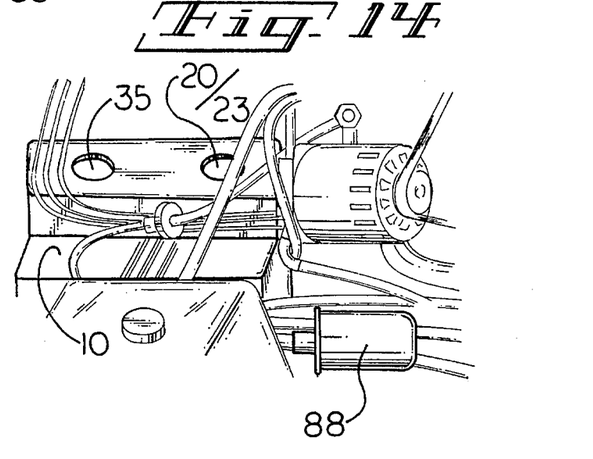
FIG. 14 is a perspective view of the part of FIG. 13 with caps for actual and mimic engine oil filling open.

Moreover, in complex, larger engines, among a plethora of lines and components, a few added automobile hoses do not appear to be out of place at all. See, FIGS. 13 & 14.

Figure 15:
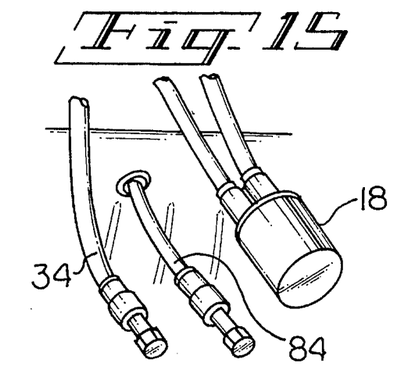
FIG. 15 is a perspective view of a further part of the clandestine engine oil sampling apparatus shown in FIGS. 13 & 14, but being that part set up in the environment of the passenger cab of the motor vehicle, minus an engine oil collection and dispersion tank.
Figure 16:
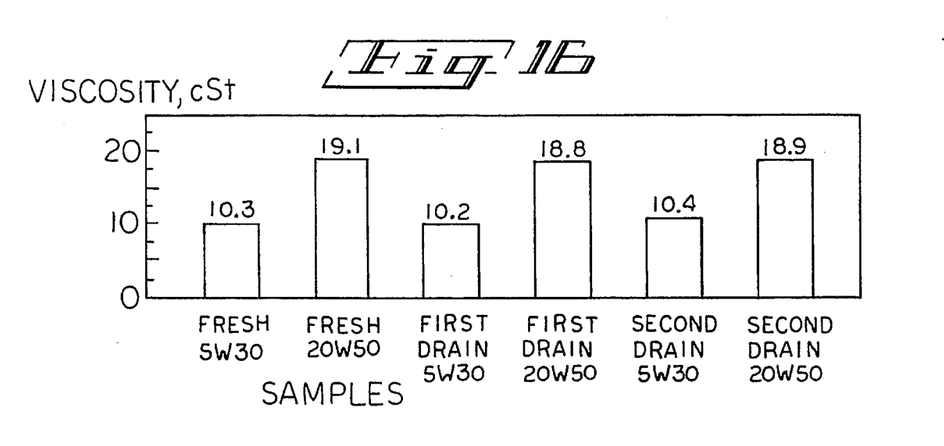
FIG. 16 is a bar graph of results of a cross-contamination study, of kinematic viscosity of oil at 100 degrees C., according to ASTM D 445, with the ordinate expressed in units of centistokes (cSt).
Figure 17:
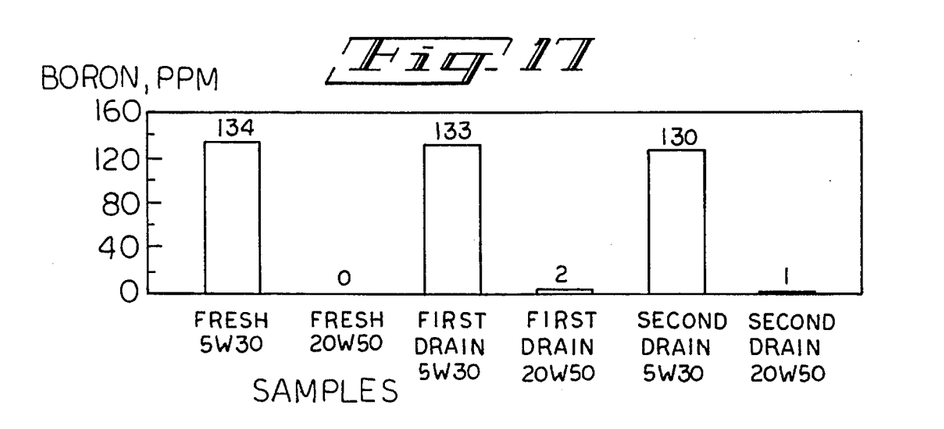
FIG. 17 is a bar graph of further results of the cross-contamination study, of boron by spectrophotometry employing inductively coupled plasma (ICP) according to ASTM D 5185, with the ordinate expressed in units of parts per million (ppm).
Figure 18:
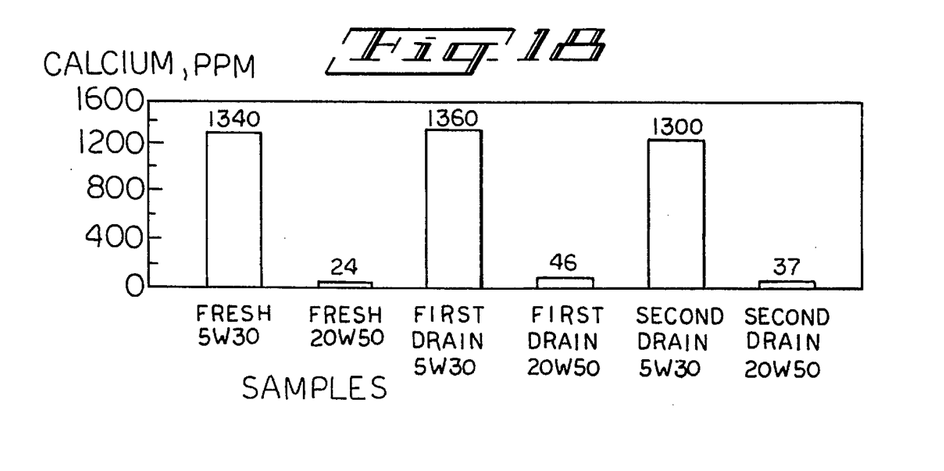
FIG. 18 is a bar graph of further results of the cross-contamination study, of calcium by ICP according to ASTM D 5185, with the ordinate expressed in units of ppm.
Figure 19:
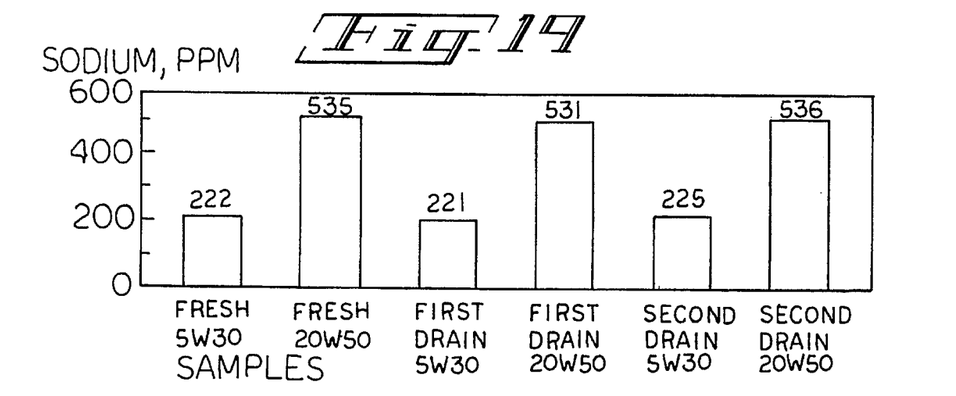
FIG. 19 is a bar graph of further results of the cross-contamination study, of sodium by ICP according to ASTM D 5185, with the ordinate expressed in units of ppm.
Figure 20:
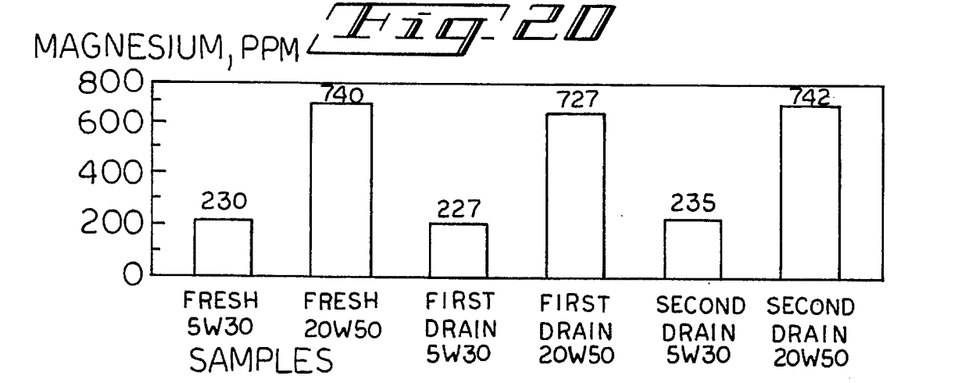
FIG. 20 is a bar graph of further results of the cross-contamination study, of magnesium by ICP according to ASTM D 5185, with the ordinate expressed in units of ppm.

Preferably also, actual oil filter 18 is present, but hidden from view from the service station attendant. It may be accessible from the passenger cab of the vehicle as depicted in FIG. 15.

The shunt line 34 can be a suitably sized, oil-resistant tubing. For example, the shunt line may be Gates 4219G full line PVC ¾-inch (190-mm) SAE 30R7 GL613193X3120 tubing.

Figure 4:
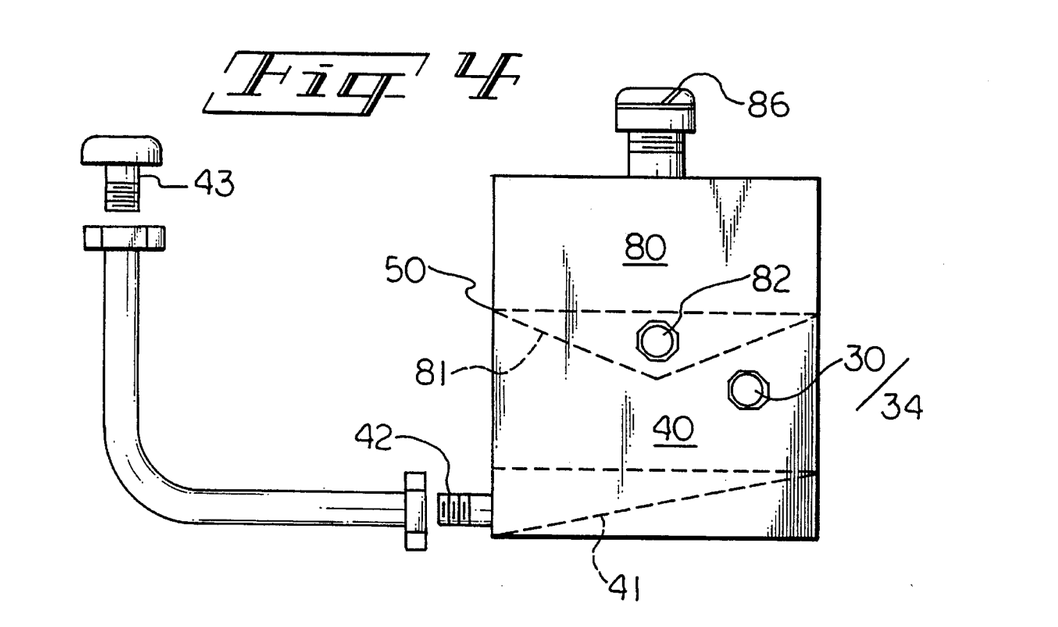
FIG. 4 is a side, partial see-through view of a combined collection and dispersion tank of the invention.
Figure 5:
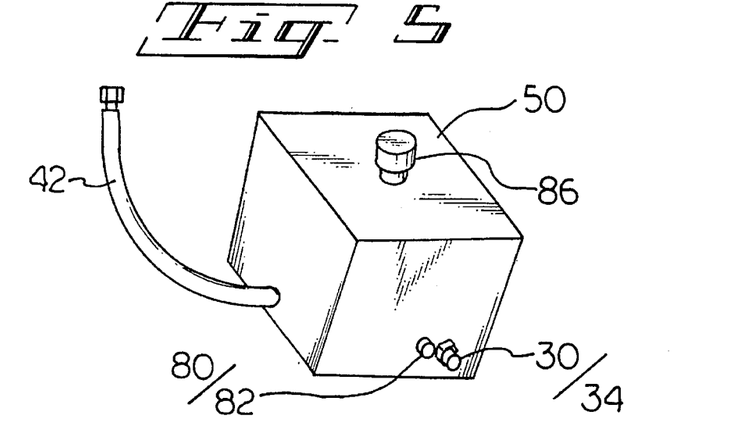
FIG. 5 is a perspective view of the tank of FIG. 4.

The shunt 30 leads, for example, by gravity flow, although an uphill flow system may be employed such as provided by siphoning and/or pumping, to entry reservoir 40, made of any suitable material to include inert plastics and metals, for example, steel, and which, for example, may have inclined floor 41 leading to sample oil drain port 42, which may be controlled by sample oil drain valve 43, and be part of larger, inside receptacle 50 as depicted in FIGS. 1, 4 & 5. The inside receptacle 50 may be in the passenger cab of the vehicle and/or be in a payload compartment thereof. Separate sample receptacles 44 may be employed to drain successive aliquots of sample oil 5 collected.

Figure 2:
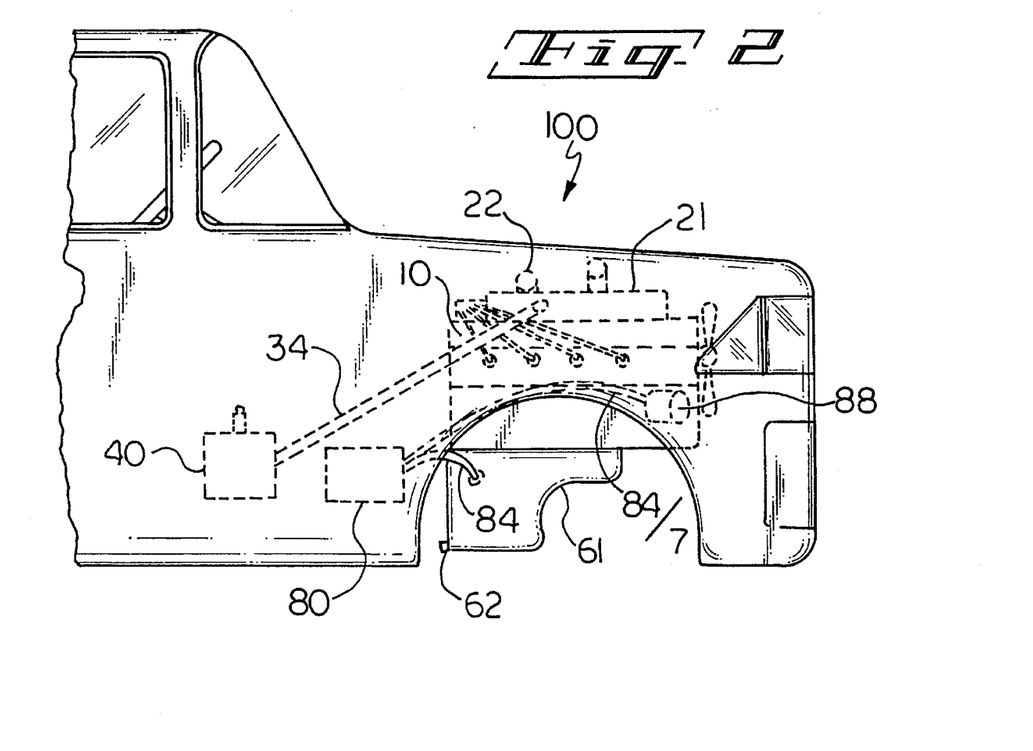
FIG. 2 is a general side view of another clandestine engine oil sampling apparatus of the invention.
Figure 3:
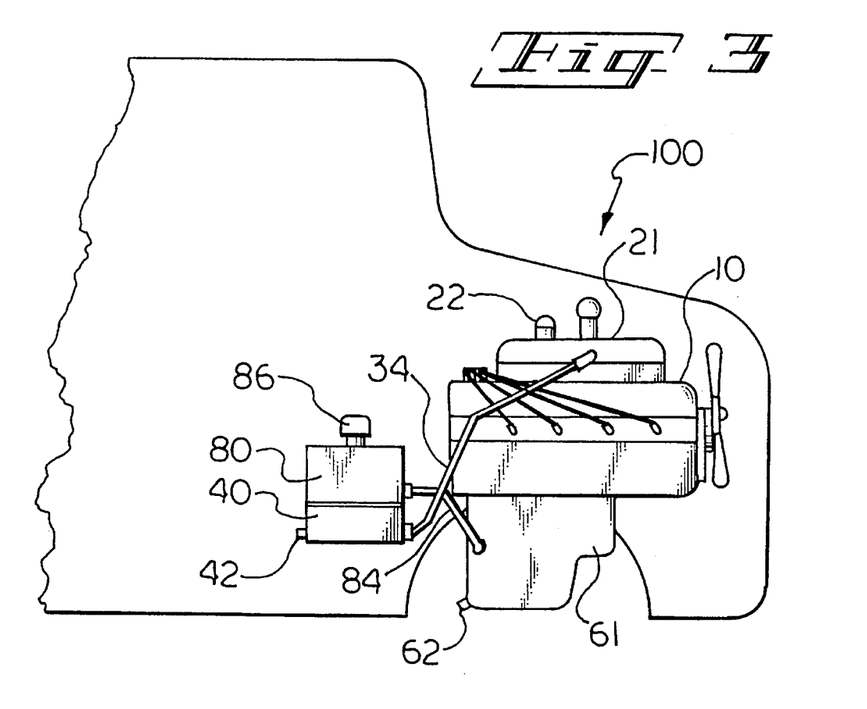
FIG. 3 is a general side view of a clandestine engine oil sampling apparatus of the invention in the environment of a motor vehicle, without showing oil filters.

In an alternative embodiment, as depicted in FIG. 2, the entry reservoir 40 is an independent, movable receptacle. It may have a longer portion to the entry shunt line 34, for example, inside the passenger cab of the vehicle, or be in a payload compartment, in order to facilitate draining and/or filling.

The entry components 20, 30 & 40 may be heated to assist in draining motor oil samples 5. This is especially helpful during cold weather.

In general, an analytically insignificant amount of the motor oil 5 remains in components 20, 30 & 40 as a "transfer quantity" when obtaining successive samples. Typically, for example, some 15–20 mL or less, preferably 10 mL or less, of a motor oil sample which has been pumped in the entry port 20 will not be drained from the entry reservoir 40. With a 5-quart oil change sample, such provides for more than adequate accuracy in oil analysis. The entry reservoir 40 typically has a 5–6 quart capacity as for a 5-quart capacity engine 10.

Optionally but preferably, the apparatus 100 also has exit port 60, exit shunt 70 and exit reservoir 80. The exit port 60 is in mimic of an oil exit port of the motor vehicle engine such as in standard-looking oil pan 61 having standard threaded oil drain plug assembly 62, e.g., with tapped bore 63, from which expendable motor oil portion 7 can drain.

In one embodiment, as depicted in FIG. 1, the exit shunt 70 can be provided with interior, exit shunt plate 71, made, for example, of a steel sheet or brass sheet welded or brazed to the interior of the oil pan 61. Interior, threaded oil drain plug bolt 72, which may be made of steel, brass, plastic, and so forth, may be releasable, after removing the threaded oil drain plug bolt 62 from tapped bore 63, by rotating the interior plug 72 by an Allen-wrench inserted in an Allen-wrench fitting, so that it opens shunt plate bore 73 to drain the working engine oil 6 privately.

Figure 6:
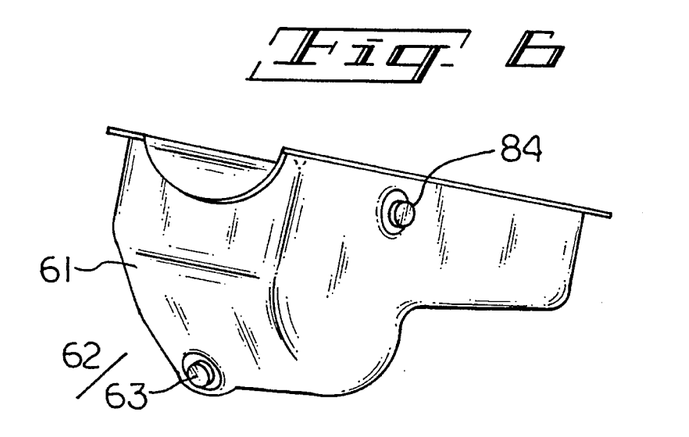
FIG. 6 is a perspective view of a modified oil pan of the invention.
Figure 7:
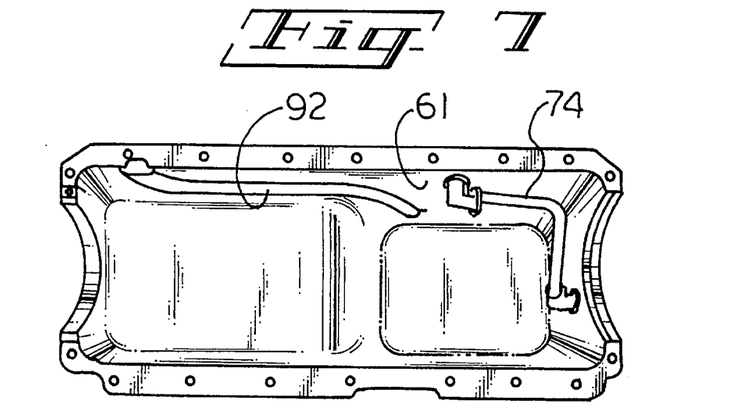
FIG. 7 is a top view of the inside of the oil pan of FIG. 6.
Figure 8:
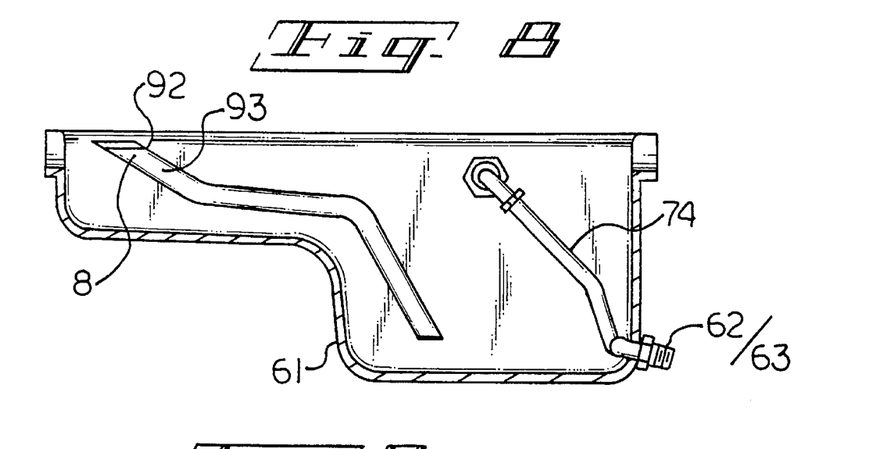
FIG. 8 is a cut-away side view of the oil pan of FIG. 6.
Figure 9:
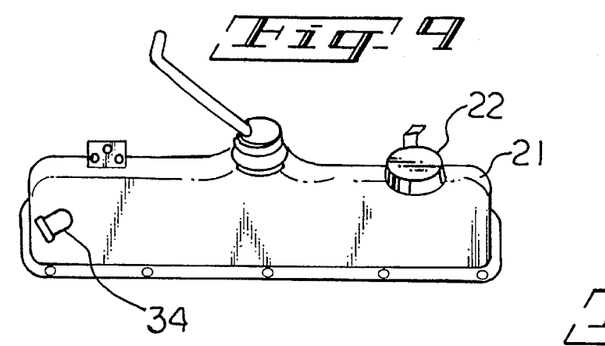
FIG. 9 is a perspective view of a modified valve cover of the invention.
Figure 10:
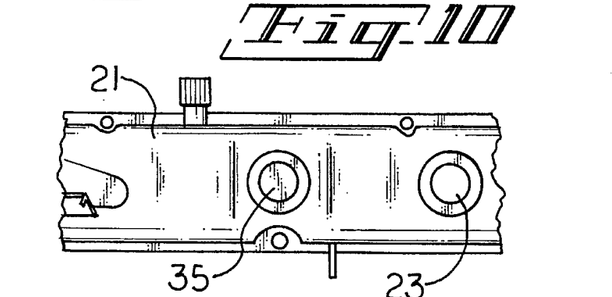
FIG. 10 is a top view of a portion of the valve cover of FIG. 9.
Figure 11:
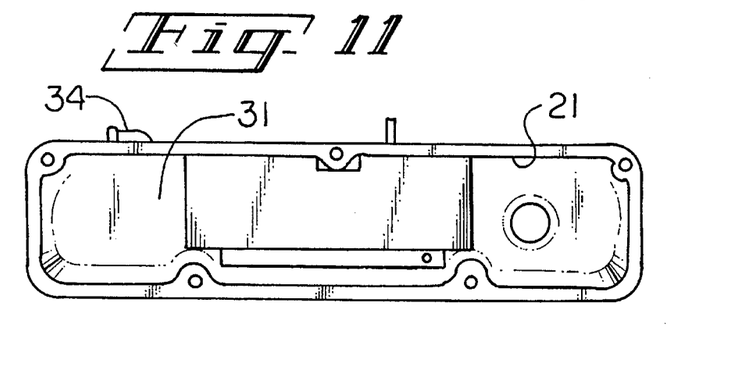
FIG. 11 is a bottom view of the inside of the cover of FIG. 9.
Figure 12:
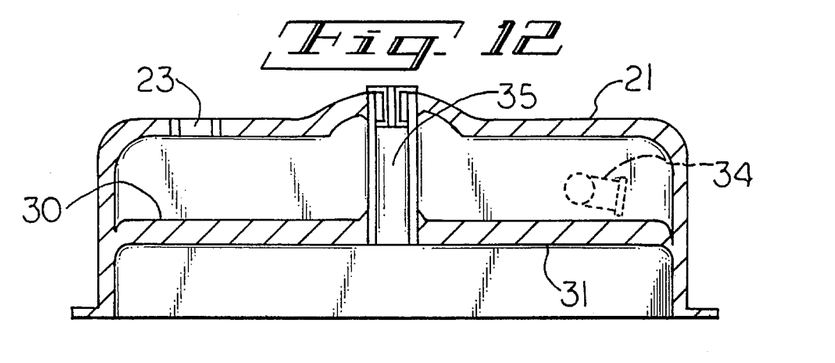
FIG. 12 is a cut-away side view of the cover of FIG. 9.

In a preferred embodiment, as depicted in FIGS. 6–8, the exit shunt 70 can be provided with interior, oil pan pipe by-pass 74. Dummy used oil can enter the by-pass 74 from the exit reservoir 80 through external by-pass connector 75.

From the exit reservoir 80, which can hold a supply of expendable oil 7 and be made of any suitable material to include inert plastics and metals, for example, steel, and which, for example, may have inclined floor 81 leading to sample oil drain port 82, and optional, though preferably absent, exit valve 83, exit line 84, made of a suitably sized, oil-resistant tubing, for example, Gates 4219G full line PVC ¾-inch (190-mm) SAE 30R7 GL613193X3120 tubing, leads, for example, by gravity flow, although, again, an uphill flow system may be employed such as provided by siphoning and/or pumping, to the exit shunt 70. The exit reservoir 80 also may be part of the larger, inside receptacle 50 as depicted in FIGS. 1, 4 & 5. Again, the inside receptacle 50 may be in the passenger cab of the vehicle and/or a payload compartment thereof.

In an alternative embodiment, as depicted in FIG. 2, the exit reservoir 80 is an independent, movable receptacle. It may have a longer portion to the exit line 84, for example, inside the passenger cab of the vehicle, or be in a payload compartment, in order to facilitate filling and/or draining.

Optionally, heater 85 may be present with the exit reservoir 80 to heat the expendable oil supply 7 so that, when it is drained from the exit port 60 as by an unwitting service attendant, the expendable oil 7 is removed from the apparatus 100 as heated to a temperature indicative of operation of the engine 10.

Advantageously, air pressure equalizer 86 is present such as can be provided by an air hole to the outside air. See, FIGS. 4 & 5.

Generally, dummy oil filter 88 is present. It may be in the usual position on the engine 10, or even be placed elsewhere in the engine compartment of the vehicle without arousing suspicion of service station attendants. See, FIGS. 13 & 14. It may have a used or expendable oil supply 7 in communication with that of the exit reservoir 80 for a more authentic mimic oil change.

The exit reservoir may hold about 4–5 quarts of expendable oil 7, for example, in mimic of a 5-quart oil capacity engine, and release it all, or it may hold more and release a part of it, for example, holding 12 quarts and releasing 3 separate 4-quart aliquots for 3 separate oil "changes" as by controlling the exit valve 83. Some expendable oil 7 may be, in addition, initially stored in the exit shunt 70 and lines in communication therewith.

Preferably as well, the apparatus 100 has dummy dipstick fill indicator device 90 having a dummy dipstick 91 and dummy dipstick sheath 92 in mimic of a dipstick fill indicator device normally on the motor vehicle engine 10. Oil reservoir 93, proximate a lower end of the dipstick sheath, can be filled with oil 8, and into the dummy dipstick device reservoir 93 the dummy dipstick 91 can be inserted so as to mock-indicate filling of the motor vehicle engine 10 with the newly-filled, sample oil 5.

The dummy dipstick device 90 need not be in communication with the fresh sample oil supply 5 contained in other components of the invention so as to measure a true oil supply. In the alternative, however, the dummy dipstick device 90 may be set with its dummy dipstick 91 and dummy oil reservoir 93 such that it can measure a true oil supply. For example, the dummy dipstick device oil reservoir 93 may be connected with the entry reservoir 40 by an optional dipstick fill transfer line 94, which transmits sample oil 5 from the entry reservoir 40 to the oil reservoir 93. With gravity transfer, simply positioning the top, full levels of the two reservoirs 40 & 93 at the same height can help insure that the dummy dipstick 91 provides an accurate reading of the amount of oil sample 5 poured in. A set of sensors and/or pumps may otherwise insure that levels of the reservoirs 40 & 93 coincide whether they are filled with the same oil supply or not.

In general, the components, and especially the interior portions of the components, of the apparatus intended for collecting the sample of motor oil 5 for analysis can be composed of generally inert, smooth faced materials such as provided by metals or alloys such as steel, copper, brass, aluminum, and so forth, by plastics to include polyethylene, polypropylene, other polyolefins, fluorinated polyolefins, nylon, rubbers, and so forth and the like. Typically, components when exposed to view resemble ordinary hoses, lines, and so forth, as could be expected to be present with or about the engine 10.

Without optional components such as 60, 70 & 80, with a clandestine oil change, working oil 6 is drained in public from the crankcase without being replaced. Although such a sparse arrangement is advantageous from the point of view of subterfuge, such an arrangement causes the engine 10 to run without a supply of working oil, which may damage the same.

In preferred use, the service attendant such as at an engine oil change facility, gains access to the exit port 60 by unscrewing drain plug 63, draining oil therefrom. Dummy oil filter 88 is changed. With its preferred arrangement, the drained oil is the expendable oil supply 7, which has flowed through the exit shunt 70 to the exit port 60, bypassing working motor oil supply 6 of the motor vehicle engine 10, which had been stored in and flows from the exit reservoir 80. Seeing the expendable oil 7 he has collected, which is preferably provided as used oil, he then opens the entry port 20, still typically unaware of the modifications to the engine. A sample of motor oil 5 is dispensed into the entry port 20, which travels through the passageways provided by the entry shunt 30 so as to bypass lubricated moving parts in the motor vehicle engine 10. Then, the sample of motor oil enters the entry reservoir 40, where it can be stored or removed later for analysis. Then in general, the service attendant, after he has pumped or poured in an amount and type of motor oil which he thinks is appropriate for the engine 10, goes to dummy dipstick 91, removes it and observes the full, clean oil mark thereon. He reports the results to the "customer," who then pays for the sample 5 and service and drives away, as the service attendant readies himself for the next customer.

Certain embodiments of the clandestine engine oil sampling apparatus of the invention have been field tested in a motor vehicle in the U.S.A., beginning in late 1993. The tested invention has been shown to be highly effective in the collection of motor oil samples, with a zero percent detection rate by engine oil service station attendants. As well, it has shown to provide for excellent accuracy for subsequent analyses of motor oil compositions.

The following examples further illustrate the invention.

EXAMPLE 1

A motor vehicle was fitted with a clandestine engine oil sampling apparatus. This is depicted in FIGS. 3–15.

A technician attempted clandestine collection of sixteen different bulk engine oil samples in the U.S.A. from various quick-change engine oil service stations through standard operations of the service station attendant. In one or more instances, the service station operator said, "Cool!" when the technician told him of the new location for the dummy oil filter, which was conveniently placed high in the engine compartment and not on the engine, in the vehicle.

In all cases, the oil and dummy filter were "changed" without detection of the sampling by the service station attendant, i.e., without the service station operator being aware that the oil he put into the oil-fill cap was being diverted into the oil collection tank for further sampling nor that the oil which he was draining was from a dummy oil supply. Each oil sample was drained from the collection tank, to be used for individual analysis.

EXAMPLE 2

Laboratory tests were conducted to establish that the clandestine engine oil sampling apparatus and the collection procedure used in Example 1 did not result in cross contamination of samples.

The technician who collected the bulk oil samples in Example 1 was asked to conduct a controlled study with two reference oils having significantly different physical and chemical properties. The oils chosen were Pennzoil Multi-Vie 5W30 and Kendall GT-1 Turbo 20W50 oils. The Institute of Materials purchased a case of each reference oil and created homogeneous samples by mixing the twelve quarts from each case in separate, clean five-gallon cans. A four-ounce sample of each of the two fresh reference oils was drawn from the proper five-gallon container as a control for analysis of kinematic viscosity and metals content. The technician filled the vehicle's "false crankcase" four times, alternating the two reference oils and collecting them from the receptacle mounted in the truck cab, following as closely as possible the procedures he used in collecting the field samples in Example 1. These four samples were analyzed for viscosity and metals content and compared to corresponding values obtained on the fresh reference oils. Results of the analyses for these six samples, for kinematic viscosity at 100 degrees C., according to ASTM D 445, and for metals content, i.e., boron, calcium, sodium and magnesium by ICP, according to ASTM D 5185, are shown in FIGS. 16–20, respectively.

The values for each reference oil—as tested fresh from the first drain and from the second drain—are nearly identical. Accordingly, little or no cross contamination of samples occurred with the bulk engine oil collection of Example 1.

ADDITIONALLY ILLUSTRATIVE EMBODIMENTS

The foregoing principles and particularized operations of the invention can be extended to cover the clandestine sampling of virtually any fluid, especially from a motor vehicle, for example, a car, truck, or even an airplane. What is done in general terms is that as a minimum a shunt, which may or may not be operator selectable, is provided to direct the fluid into a reservoir apart from the working part(s) of the fluid system under consideration. That is to say, the fluid to be sampled is disbursed into a normal looking entry-port, from whence it enters an entry shunt in communication with the entry port, through which the sample of fluid can travel upon entry through the entry port and bypass the working part(s) to include standard reservoir(s) for the corresponding fluid (such as, for example, a washer fluid tank, a gas tank or diesel or other fuel or additive tank, a radiator, a brake fluid reservoir, a transmission or differential box or reservoir, a greased bearing unit, and so forth) and from thence it enters a sample or entry reservoir in communication with the entry shunt; and the sampled fluid is retained and passes through a sampling system which is separate from the working fluid system so as to avoid contamination thereof, thereby, during sampling.

Figure 21:
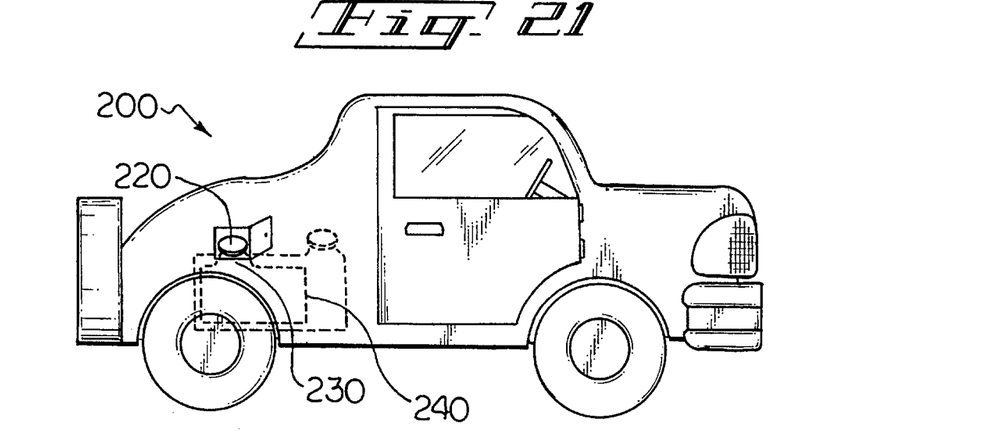
FIG. 21 is a general side view of another clandestine sampling apparatus of the invention, for collecting motor vehicle fuel.

Accordingly, in addition to the foregoing engine oil sampling apparatus of the invention, and so forth, can be provided, for example, clandestine transmission fluid sampling apparatus of the invention by analogy to the clandestine engine oil sampling apparatus of the invention. As well along such lines, in FIG. 21 is depicted a clandestine motor vehicle fuel sampling apparatus of the invention 200 having entry port 220 in mimic of the usual looking entry port for typical fueling, entry shunt 230, and entry reservoir 240, separate from any normal working fuel supply system.

Accordingly, the fluid can be sampled from any suitable object, to include stationary motors, generators, ground fuel supplies, water supplies, and so forth. Motor vehicles are advantageous objects since they can be locomoted to a number of locations to obtain various and sundry samples effectively. Along such lines, movable generators and lawn mowers and lawn and farm tractors are also likely candidates for the object.

CONCLUSION

The present invention is thus provided. Numerous modifications can be effected within its spirit, the literal claim scope of which is particularly pointed out as follows:

We claim:

1. A clandestine engine oil sampling apparatus comprising an engine for a motor vehicle with the following components: an entry port in mimic of an oil entry port of the engine into which a sample of motor oil can be dispensed; an entry shunt in communication with the entry port in mimic of an oil entry port of the engine, through which entry shunt the sample of motor oil can travel upon entry through the entry port in mimic of an oil entry port of the engine and bypass lubricated moving parts in the engine; and an entry reservoir in communication with the entry shunt, in which the sample of motor oil can be stored upon travel through the entry shunt, and the sample of motor oil is separate from working and storage systems of the engine.

2. The apparatus of claim 1, further comprising an exit port in mimic of an oil exit port of the engine from which exit port in mimic of an oil exit port of the engine an expendable motor oil portion can drain; an exit shunt in communication with the exit port in mimic of an oil exit port of the engine, through which the expendable motor oil portion can flow to the exit port in mimic of an oil exit port of the engine, apart from any working motor oil supply of the engine; and an exit reservoir in communication with the exit shunt, in which the expendable motor oil portion can pass through into the exit shunt and at least a portion of which can be stored for release into the exit shunt; and a dipstick fill indicator device having a dipstick and dipstick sheath in mimic of a dipstick fill indicator device of the engine, with an oil reservoir in communication with a lower end of the dipstick sheath, which can be filled with oil and into which the dipstick can be inserted so as to indicate mock-filling of the engine with new oil.

3. The apparatus of claim 1, further comprising a motor vehicle in which the engine is mounted, wherein the entry reservoir is inside a passenger or payload compartment of the vehicle.

4. The apparatus of claim 2, further comprising a motor vehicle in which the engine is mounted, wherein the entry and exit reservoirs are inside a passenger or payload compartment of the vehicle.

5. The apparatus of claim 4, wherein the entry and exit reservoirs are part of a larger, inside receptacle.

6. The apparatus of claim 4, wherein the entry and exit reservoirs are independent and movable from another.

7. The apparatus of claim 1, wherein an analytically insignificant amount of motor oil can remain as a transfer quantity in the entry port in mimic of an oil entry port of the engine, in the entry shunt, and in the entry reservoir.

8. The apparatus of claim 3, wherein an analytically insignificant amount of motor oil can remain as a transfer quantity in the entry port in mimic of an oil entry port of the engine, in the entry shunt, and in the entry reservoir.

9. A method for clandestinely sampling a motor oil comprising operation of a clandestine engine oil sampling apparatus, which includes a vehicle having an engine mounted therein, which engine includes the following components: an entry port in mimic of an oil entry port of the engine into which a sample of motor oil can be dispensed; an entry shunt in communication with the entry port in mimic of an oil entry port of the engine, through which entry shunt the sample of motor oil can travel upon entry through the entry port in mimic of an oil entry port of the engine and bypass lubricated moving parts in the engine; and an entry reservoir in communication with the entry shunt, in which the sample of motor oil can be stored upon travel through the entry shunt, and the sample of motor oil is separate from working and storage systems of the engine.

10. The method of claim 9, wherein the engine further includes an exit port in mimic of an oil exit port of the engine from which exit port in mimic of an oil exit port of the engine an expendable motor oil portion can drain; an exit shunt in communication with the exit port in mimic of an oil exit port of the engine, through which the expendable motor oil portion can flow to the exit port in mimic of an oil exit port of the engine, apart from any working motor oil supply of the engine; and an exit reservoir in communication with the exit shunt, in which the expendable motor oil portion can pass through into the exit shunt and at least a portion of which can be stored for release into the exit shunt; and a dipstick fill indicator device having a dipstick and dipstick sheath in mimic of a dipstick fill indicator device of the engine, with an oil reservoir in communication with a lower end of the dipstick sheath, which can be filled with oil and into which the dipstick can be inserted so as to indicate mock-filling of the engine with new oil.

11. The method of claim 10, wherein a service station attendant changes oil unaware that the oil put in is for sampling purposes.

12. A clandestine fluid sampling apparatus comprising an object which would receive fluid with the following components: a fluid entry port in mimic of a fluid entry port of the object into which a sample of the fluid can be dispensed; an entry shunt in communication with the entry port, through which the sample of fluid can travel upon entry through the entry port and bypass any working part(s) or standard reservoir(s) for the fluid in the object; and an entry reservoir in communication with the entry shunt, in which the sample of fluid can be stored upon travel through the entry shunt, wherein the aforesaid components, as a system, are separate from working and storage systems, to include any fluid system, of the object.

13. The apparatus of claim 12, wherein the object is a motor vehicle.

14. The apparatus of claim 12, wherein an analytically insignificant amount of the fluid can remain as a transfer quantity in the fluid entry port, in the entry shunt, and in the entry reservoir.

15. The apparatus of claim 13, wherein the fluid is a fuel.

* * * * *